(12) United States Patent
Yang et al.

(10) Patent No.: US 9,695,218 B2
(45) Date of Patent: Jul. 4, 2017

(54) PHARMACEUTICAL COMPOSITION FOR PREVENTING OR TREATING OCULAR SURFACE DISEASE

(71) Applicant: INJE UNIVERSITY INDUSTRY-ACADEMIC COOPERATION FOUNDATION, Gyeongsangnam-do (KR)

(72) Inventors: Jae Wook Yang, Busan (KR); Hye Sook Lee, Busan (KR); Ji Hyun Lee, Busan (KR); Yoon Jin Lee, Busan (KR)

(73) Assignee: INJE UNIVERSITY INDUSTRY-ACADEMIC COOPERATION FOUNDATION, Gimhae-si, Gyeongsangnam-Do (KR)

( * ) Notice: Subject to any disclaimer, the term of this patent is extended or adjusted under 35 U.S.C. 154(b) by 0 days.

(21) Appl. No.: 14/979,511

(22) Filed: Dec. 27, 2015

(65) Prior Publication Data

US 2016/0215018 A1  Jul. 28, 2016

(30) Foreign Application Priority Data

Dec. 26, 2014 (KR) ........................ 10-2014-0190726

(51) Int. Cl.
| | |
|---|---|
| *C07K 7/06* | (2006.01) |
| *A61P 27/06* | (2006.01) |
| *C07K 14/78* | (2006.01) |
| *A61K 38/00* | (2006.01) |
| *A61K 9/00* | (2006.01) |

(52) U.S. Cl.
CPC ............... *C07K 7/06* (2013.01); *C07K 14/78* (2013.01); *A61K 9/0048* (2013.01); *A61K 38/00* (2013.01)

(58) Field of Classification Search
None
See application file for complete search history.

(56) References Cited

FOREIGN PATENT DOCUMENTS

KR    10-2010-0029672 A    3/2010

OTHER PUBLICATIONS

Corneal Disease, NIH, Nat'l Eye Inst. accessed Oct. 14, 2016 at URL nei.nih.gov/health/cornealdisease, pp. 1-13.*
Scleritis, Merck Manual, accessed Oct. 14, 2016 at URL merckmanuals.com/professional/eye-disorders/conjunctival-and-scleral-disorders/scleritis, pp. 1-4.*
Corneal Ulcer, Merck Manual, accessed Oct. 14, 2016 at URL merckmanuals.com/home/eye-disorders/corneal-disorders/corneal-ulcer, pp. 1-3.*
McAlinden et al., "Missense and Nonsense Mutations in the Alternatively-Spliced Exon 2 of COL2A1 Cause the Ocular Variant of Stickler Syndrome," Hum. Mut. 29:83-90 (2008).*

* cited by examiner

*Primary Examiner* — Julie Ha
*Assistant Examiner* — Kristina M Hellman
(74) *Attorney, Agent, or Firm* — Revolution IP, PLLC

(57) ABSTRACT

A pharmaceutical composition for preventing or treating an ocular surface disease is disclosed, wherein the pharmaceutical composition includes, as an active component, collagen type II α1 based peptide SEQ ID NO: 2 isolated from chondrocyte-derived extracellular matrix (CDEM). In an alkaline burn animal mode treated with peptide SEQ ID NO: 2, the occurrence of corneal opacification is reduced as well as the expression of angiogenic factors. In addition, the expression of inflammatory markers is reduced while the expression of inflammation-inducing factor is suppressed. The peptide SEQ ID NO: 2 may be applied to a pharmaceutical composition for preventing or treating an ocular surface disease.

3 Claims, 6 Drawing Sheets
(1 of 6 Drawing Sheet(s) Filed in Color)

(A)

(B)

PHARMACEUTICAL COMPOSITION FOR PREVENTING OR TREATING OCULAR SURFACE DISEASE

RELATED APPLICATION

This application claims the benefit of Korean Patent Application No. 10-2014-0190726, filed on Dec. 26, 2014, in the Korean Intellectual Property Office, the disclosure of which is incorporated herein in its entirety by reference.

BACKGROUND

1. Field

The present disclosure relates to a pharmaceutical composition for preventing or treating ocular surface disease, the pharmaceutical composition including a novel peptide as an active component.

2. Description of the Related Art

The ocular surface is a specialized body surface consisting of conjunctival epithelial cells and corneal epithelial cells. These cells constitute a healthy ocular surface with tears secreted from main and accessory lacrimal glands, and such a healthy ocular surface is essential for optimal functions of the eyes.

The cornea is a transparent and avascular tissue occupying about ⅙ of a front surface of the eyes. Corneal nerves are developed since the cornea is responsible for not only protecting the eyes from the outside, but also performing key features regarding light refraction and transmission. The cornea has five layers including corneal epithelium, Bowman's layer, corneal stroma, descemet's membrane, and corneal endothelium. The corneal epithelium cells occupy about 10% of the thickness of the entire cornea, and are continuous with the conjunctival epithelium and are composed of about 5 to 7 layers of cells which are shed away about 7 to 14 days after proliferation in the basal layer.

Corneal lesion is one of the most frequently diagnosed diseases, and is a main cause of visual impairment. Corneal lesion may be caused by various reasons, and for example, may be mainly caused by allergies, infections, dry eyes, surgical operations, or other traumas. In the case of corneal injury or disease, the original state of the corneal is destroyed. Corneal injury may stimulate lateral movement of corneal epithelial cells, which are believed to be provided from limbal stem cells, infiltration of inflammatory cells, and angiogenesis in the injured stroma. Furthermore, corneal angiogenesis, inflammation, and chemical injuries on the cornea may adversely affect transparency of the eyes and may subsequently cause the loss of sight, requiring prompt treatment. However, therapeutic agents that are currently commercially available for ocular surface diseases may include steroids or non-steroidal inflammatory agents, but the steroids or non-steroidal inflammatory agents are used only as relaxants.

PRIOR ART DOCUMENT

Patent Document

KR 2010-0029672

SUMMARY

Provided is a collagen type II α1 based peptide isolated from chondrocyte-derived extracellular matrix (CDEM).

Provided is a pharmaceutical composition for preventing or treating an ocular surface disease, the pharmaceutical composition including the collagen type II α1 based peptide.

Additional aspects will be set forth in part in the description which follows and, in part, will be apparent from the description, or may be learned by practice of the presented exemplary embodiments.

According to an aspect of an exemplary embodiment, a peptide includes an amino acid sequence of SEQ ID NO: 2.

According to an aspect of another exemplary embodiment, a pharmaceutical composition for preventing or treating an ocular surface disease includes, as an active component, a peptide having an amino acid sequence of SEQ ID NO: 2

The peptide represented by SEQ ID NO: 2 may be a collagen type II α1 based peptide isolated from CDEM.

The ocular surface disease according to the present invention may be one of corneal opacification, corneal angiogenesis, corneal inflammation, and corneal fibrosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects will become apparent and more readily appreciated from the following description of the exemplary embodiments, taken in conjunction with the accompanying drawings in which.

DETAILED DESCRIPTION

Figure 1:
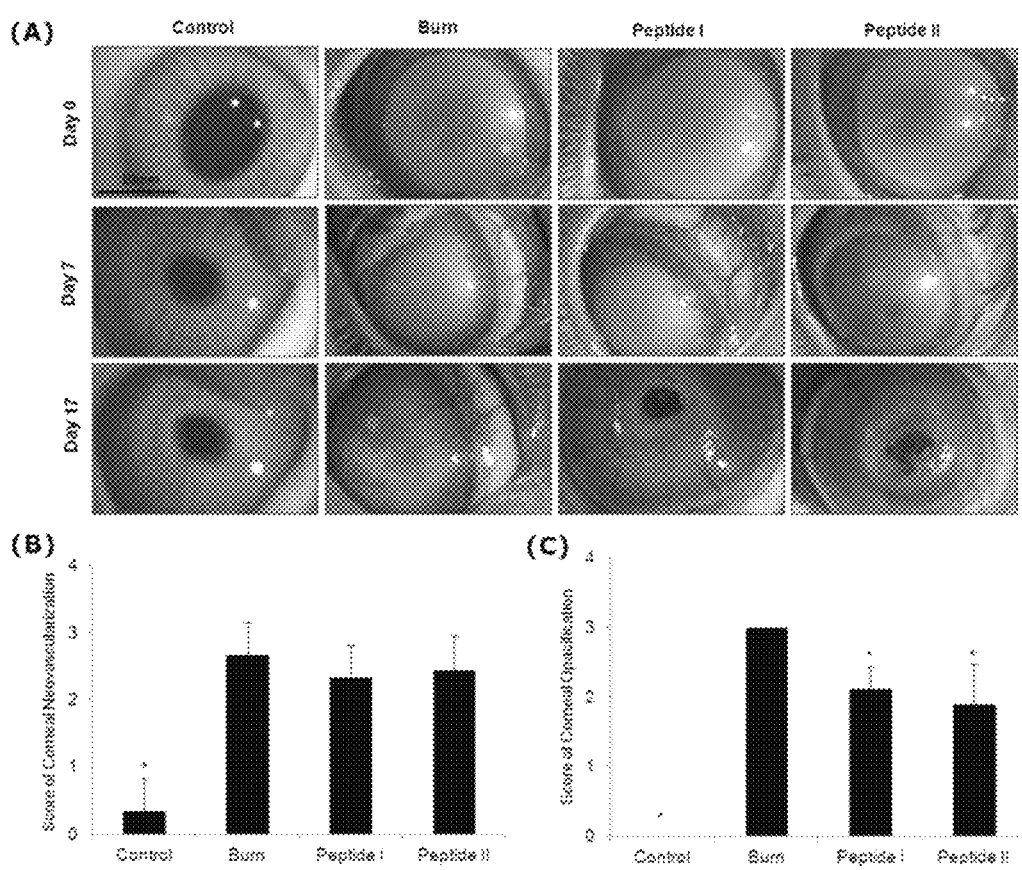
FIG. 1 shows results confirming effects of SEQ ID NO: 2 on cornea of an alkaline burn rabbit, wherein (A) of FIG. 1 shows photographs of rabbit corneas at 0, 7, and 17 days after alkaline burn as being obtained with a microscope (SZX7, Olympus, Tokyo, Japan) (scale bar=10 mm), (B) of FIG. 1 shows graphs presenting extents of corneal angiogenesis, and (C) of FIG. 1 shows graphs presenting extents of corneal opacification, wherein the graph data are expressed as the mean±standard deviation (n=5) in terms of statistical significance by t-test at *$P<0.05$ vs alkaline burn group.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

In an exemplary embodiment of the present invention, there is provided a peptide having an amino acid sequence of SEQ ID NO: 2.

In another exemplary embodiment of the present invention, there is provided a pharmaceutical composition for treating or preventing an ocular surface disease, the pharmaceutical composition including, as an active component, the peptide having the amino acid sequence of SEQ ID NO: 2.

The peptide having the amino acid sequence of SEQ ID NO: 2 according to the present invention may be collagen type II α1 based peptide isolated from chondrocyte-derived extracellular matrix (CDEM).

In particular, CDEM may be isolated from a CDEM that are formed as being secreted from a cartilage tissue and/or a chondrocyte of an animal. The animal may be one of pigs, horses, cattle, sheep, goats, and monkeys, but the animal is not limited thereto.

The ocular surface disease according to the present invention may be one of corneal opacification, corneal angiogenesis, corneal inflammation, and corneal fibrosis, but the ocular surface disease is not limited thereto.

The peptide having the amino acid sequence of SEQ ID NO: 2 according to the present invention may be included an amount ranging from about 0.1 to about 50 parts by weight based on a total of 100 parts by weight of the pharmaceutical composition.

The pharmaceutical composition may be formulated as one of eye drops, injections, granules, tablets, pills, capsules, gels, syrups, suspensions, emulsions, drips, and liquids, but the formulation is not limited thereto.

In another exemplary embodiment of the present invention, the pharmaceutical composition including, as an active component, the peptide having the amino acid sequence of SEQ ID NO: 2 for preventing or treating an ocular surface disease may further include at least one appropriate additive selected from carriers, excipients, disintegrating agents, sweetening agents, coating agents, swelling agents, glidants, flavoring agents, antioxidants, buffers, bacteriostatic agents, diluents, dispersants, surfactants, binders, and lubricants that are typically used in preparation of a composition in the art.

In further detail, examples of the carriers, the excipients, and diluents include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. Examples of solid formulations for oral administration include tablets, pills, powders, granules, and capsules. Such solid formulations may be prepared by mixing the pharmaceutical composition with at least one excipient, e.g., starch, calcium carbonate, sucrose or lactose, or gelatin. Also, a lubricant such as magnesium stearate or talc may be used in addition to a simple excipient. Examples of the liquids for oral administration include suspensions, material solutions, emulsions, and syrups, and the liquids may further include various types of excipient including wetting agents, sweeteners, flavoring agents and preservatives, in addition to simple and commonly used diluents, such as water or liquid paraffin. Examples of formulations for parenteral administration include sterilized aqueous solutions, non-aqueous solvents, suspensions, emulsions, lyophilized preparations, and suppositories. Examples of the non-aqueous solvents and the suspensions include propylene glycol, polyethylene glycol, vegetable oil including olive oil, and injectable esters including ethyl oleate. Bases for the suppositories may be witepsol, macrogol, tween 61, cacao butter, Laurin, or glycerogelatine.

In an exemplary embodiment of the present invention, the pharmaceutical composition may be administered to a subject via a conventional route of administration selected from intravenous, intraarterial, intraperitoneal, intramuscular, intrasternal, percutaneous, intranasal, inhalation, topical, rectal, oral, intraocular, or subcutaneous administration.

A desired dose of the peptide having the amino acid sequence of SEQ ID NO: 2 to a subject may differ according to the subject's conditions and weight, types and severity of a disease, a drug form, an administration route, and an administration period, and may be appropriately selected by one of ordinary skill in the art. In an exemplary embodiment of the present invention, a daily dose of the peptide having the amino acid sequence of SEQ ID NO: 2 may be in a range of about 0.01 to about 200 mg/kg, for example, about 0.1 to about 200 mg/kg, for example, about 0.1 to about 100 mg/kg, but the daily dose is not limited thereto. Administration may be performed once a day or several times a day, but the number of administration is not limited thereto.

The term 'subject' as used herein may refer to mammals including humans, but the 'subject' is not limited thereto.

Hereinafter, the present invention will now be described more fully with reference to exemplary embodiments below. The present invention may, however, be embodied in many different forms and should not be construed as being limited to the exemplary embodiments set forth herein; rather, these embodiments are provided so that this disclosure will be thorough and complete, and will fully convey the concept of the inventive concept to those skilled in the art.

<Experimental Example 1> Immunohistochemical Analysis

Ocular tissue sections of an alkaline burn animal model were cut to a thickness of 6 μm, and then, the tissue sections were used for immunohistochemical analysis.

First, the tissue sections were fixed in 3.5% paraformaldehyde, permeabilized with 0.1% Triton X-100, blocked with 2% bovine serum albumin (BSA; all from Sigma, St.

Louis, Mo.), and incubated overnight with the following primary antibodies; anti-CD31 (1:1,000; Abcam Inc., Cambridge, Mass.), anti-MMP-9, anti-ICMA-1, anti-VCAM-1 (1:1,000; from Bioss Antibodies, Woburn, Mass.), anti-TNFα, anti-NF-κB (1:1,000; all from biorbyt LLC, San Franciso, Calif.) anti-macrophage/monocyte (Abnova Crop., Taipei, Taiwan), and anti-VEGF-A (Abbiotec, San Diego, Calif.).

Next, the tissue sections were incubated with a secondary antibody for 45 minutes. The immunological reactions therein were visualized with diaminobenzidine (DAB) chromogen, and the tissue sections were counterstained with Mayer's hematoxylin (Sigma) for 30 seconds at room temperature.

The sections were photographed with a virtual microscope (virtual microscope; NanoZoomer 2.0 RS, Hamamatsu, Japan).

<Example 1> Confirmation of Major Peptides Obtained from CDEM

Protein analysis was carried out based on a CDEM composite. The analysis of major proteins of CDEM carried out at Baek's group of Center of Biomedical Mass Sepctrometry (Diatech Korea Co., Ltd., Seoul, Korea).

As a result, as shown in Table 1, three major proteins were isolated, wherein collagen type II α1 based peptide sequence SEQ ID NO: 2 (Peptide II) possessed the highest amount as 15.9% of total proteins, followed by collagen type I α1 based peptide sequence SEQ ID NO: 3 (Peptide III) having an amount of 2.1%, and collagen type I α1 based peptide sequence SEQ ID NO: 2 (Peptide I) having an amount of 0.6%.

Accordingly, the effects of major peptide SEQ ID NO: 2 were confirmed in the alkaline burn rabbit model and compared with peptide SEQ ID NO: 1 having the lowest amount.

Peptides I to III synthesized from PEPTRon (Daejeon, Korea) were used in all experiments.

TABLE 1

| Peptide sequence | Protein | Molecular weight (kDa) | Amount (%, w/w) |
|---|---|---|---|
| Peptide I (SEQ ID NO: 1) | GDRGD | Collagen type I, α1 | 15.250 | 0.6 |
| Peptide II (SEQ ID NO: 2) | GQDGLAGPK | Collagen type II, α1 | 130.084 | 15.9 |
| Peptide III (SEQ ID NO: 3) | GPAGPR | Collagen type I, α1 | 129.160 | 2.1 |

<Example 2> Preparation of Corneal Alkaline Burn Animal Model

Experiments on animals were performed according to the guidelines for animal experiments of Inje University College of Medicine (No.; 2014-027) and the ARVO statement for the use of animals in ophthalmic and vision research.

15 New Zealand white rabbits weighing between 2.0 kg and 2.5 kg were purchased from Samtako (Osan, Korea), and then, were subjected to systemic anesthesia by intramuscular injection of a mixture of ketamine hydrochloride (30 mg/kg body weight, Huons, Jecheon, Korea) and xylazine hydrochloride (2.5 mg/kg, Bayer Korea Ltd., Seoul, Korea) and to topical anesthesia by Alcaine propracaine eye drops (Alcon Inc., Seoul, Korea).

Afterwards, alkaline burn model was developed by applying an 8 mm filter paper soaked in 1 N NaOH to the right central corneas of rabbits for 1 minute. 7 days later, an increase in corneal angiogenesis and corneal opacity upon alkaline burns was confirmed.

The rabbits were randomly divided into three groups: the alkaline burn group (n=5), the peptide I group (n=5), and the peptide II group (n=5). The alkaline burn group was treated with saline instilled thereto 4 times per day, the peptide I group was treated with 10 mg/mL of peptide SEQ ID NO: 1 instilled thereto 4 times per day, and the peptide II was treated with 10 mg/mL of peptide SEQ ID NO: 2 instilled thereto 4 times per day. The left eyes were used as controls.

On the $10^{th}$ day after the treatment as described above, the H&E staining, the Masson's trichrome staining, and immunohistochemistry were performed to observe the fibrosis, angiogenesis, inflammation, and structural changes of the cornea.

<Example 3> Confirmation of Corneal Angiogenesis and Opacification in the Corneal Alkaline Burn Rabbit Model 7 days after the corneal alkaline burns, clinical evaluation of corneal angiogenesis and opacification was performed.

First, the extent of corneal angiogenesis was scored from 0 through 3, where 0 denotes no angiogenesis, 1 denotes angiogenesis confined to the corneal periphery, 2 denotes angiogenesis extending up to the pupil margin, and 3 denotes angiogenesis extending beyond the pupil margin into the central cornea. In eyes where significant opacification or extensive symblepharon formation caused difficulties in evaluating corneal angiogenesis, a score of 3 was assigned.

In addition, the severity of corneal opacification was graded from 0 through 3, where 0 denotes clear cornea with iris details clearly visualized, 1 denotes partial obscuration of the iris details, 2 denotes iris details poorly seen with the pupil margin just visible, and 3 denotes complete obscuration of iris and pupil details.

Consequently, as shown in (A) of FIG. 1, it was confirmed that the corneal opacity immediately appeared by alkaline injury, and at the $7^{th}$ day of the alkaline burn, an increase in corneal angiogenesis and opacity following alkaline burns was observed.

In addition, following the confirmation of corneal angiogenesis and opacity, on day 17 after the alkaline burn, treatment of saline, peptide I, or peptide II was performed for 10 days. As shown in (B) and (C) of FIG. 1, the corneal opacity scores significantly increased to 3.0±0.0, with angiogenesis extending beyond the pupil margin into the central cornea 2.7±0.5 in the control group.

Meanwhile, as shown in (C) of FIG. 1, it was confirmed that the opacity decreased by peptide II 1.9±0.6 (p<0.05) and peptide I 2.1±0.3 (p<0.05), and as shown in (B) of FIG. 1, decreased angiogenesis was confirmed in the peptide II group compared to the control group.

Accordingly, it was confirmed that peptide SEQ ID NO: 2 had effects on suppressing opacification.

<Example 4> Confirmation of Effects of Peptide SEQ ID NO: 2 on Thickness Changes in Corneal Alkaline Burn Rabbit Model The corneal thickness of the tissue sections was measured using photographs obtained by the H&E staining and taken with a virtual microscope (NanoZoomer 2.0 RS, Hamamatsu, Japan) according to the NDP view program (Hamamatsu, USA).

Figure 2:
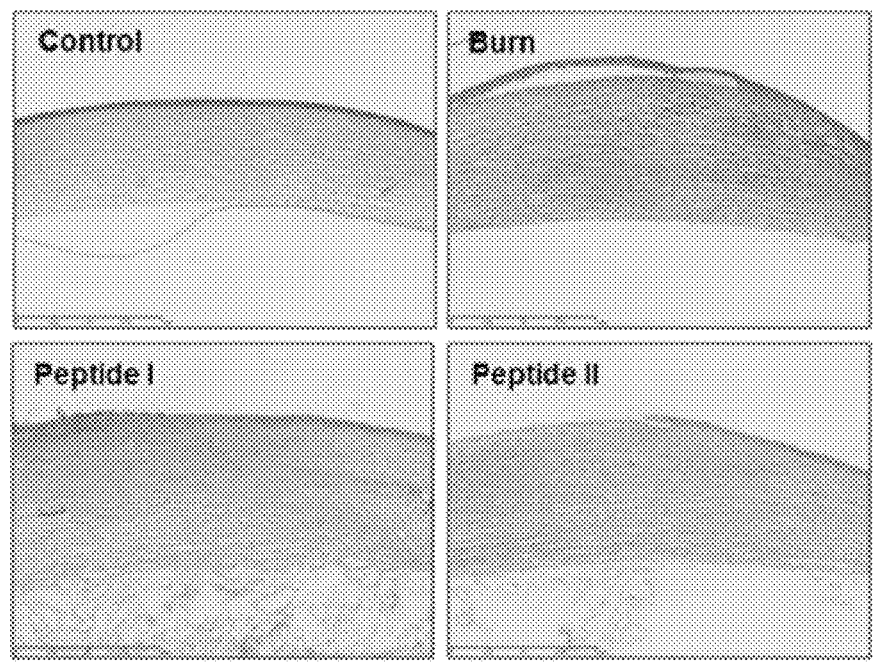
FIG. 2 shows results confirming effects of SEQ ID NO: 2 on changes in corneal thickness of the alkaline burn rabbit, wherein (A) of FIG. 2 shows images of tissue sections as being photographed with a virtual microscope (NanoZoomer 2.0 RS, Hamamatsu, Japan) (scale bar=1 mm), and (B) of FIG. 2 shows graphs presenting corneal thicknesses.
Figure 2:
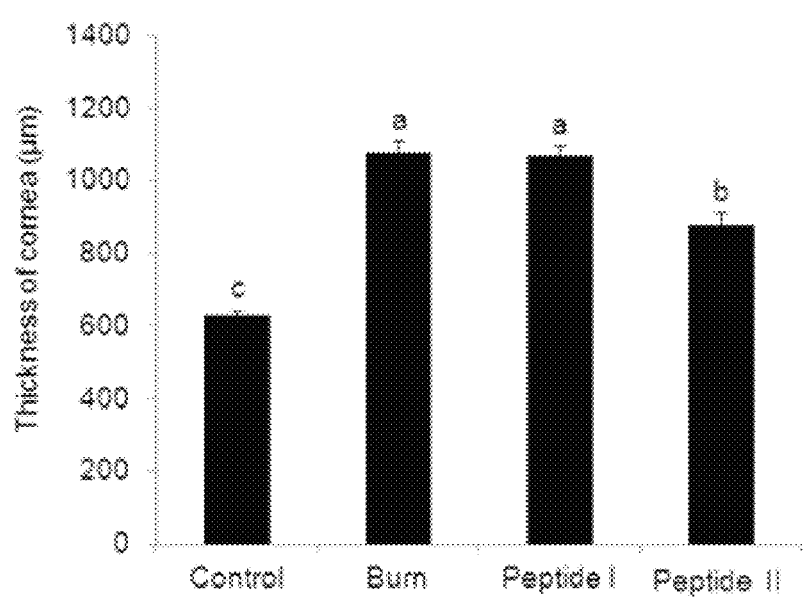

Consequently, as shown in FIG. 2, it was confirmed that the corneal thickness increased from a normal value of 628.0±13.2 μm to 1078.0±30.8 μm following the alkali burn. However, at the 10$^{th}$ day after peptide II treatment, it was confirmed that the corneal thickness decreased to 876.0±37.0 μm (p<0.05), which was lower than the control group. In contrast, the corneal thickness in the peptide I group was 1066.0±31.7 μm, which was not decreased compared with the control group.

<Example 5> Confirmation of Effects of SEQ ID NO: 2 on Fibrotic Changes in Rabbit Cornea Following Alkali Burns To confirm the fibrotic changes of the cornea in response to alkali burns, the Masson's trichrome staining was performed.

Excised eyes were fixed in 3.5% paraformaldehyde, washed, and then, stored in 70% alcohol until paraffin-embedded tissue sections were prepared to a thickness of 6 μm. To visualize the collagen fibers and grade degree of fibrosis, the sections were stained with a Massons trichrome stain kit (Polysciences, Inc. Germany) for the Massons trichrome staining. In detail, xylene was used to perform a deparaffin process on the tissue sections. The tissue sections were subjected to a hydrous process using 100% ethanol twice, 95% ethanol once, and 85% ethanol once, subsequently in the stated order, and then, washed with distilled water. Next, the tissue sections were incubated in a bouin solution at a temperature of 56° C. for 1 hour, cleaned with water for 10 minutes, and then, reacted in a weigert iorn hematoxylin working solution for 10 minutes. After washing with water, the tissue sections were reacted in a biebrich scarlet-acid fuchsin solusion for 5 minutes, washed with distilled water, and then, reacted in phosphotungstic/phosphomolybdic acid for 10 minutes. The tissue sections were stained with an aniline blue solution for 5 minutes, cleaned with water, immerged in 1% acetic acid for a minute, and then, washed subsequently with a discard solution and distilled water. Lastly, following dehydration process, transparent and mounted tissues were photographed with using a virtual microscope (NanoZoomer 2.0 RS, Hamamatsu, Japan).

Figure 3:
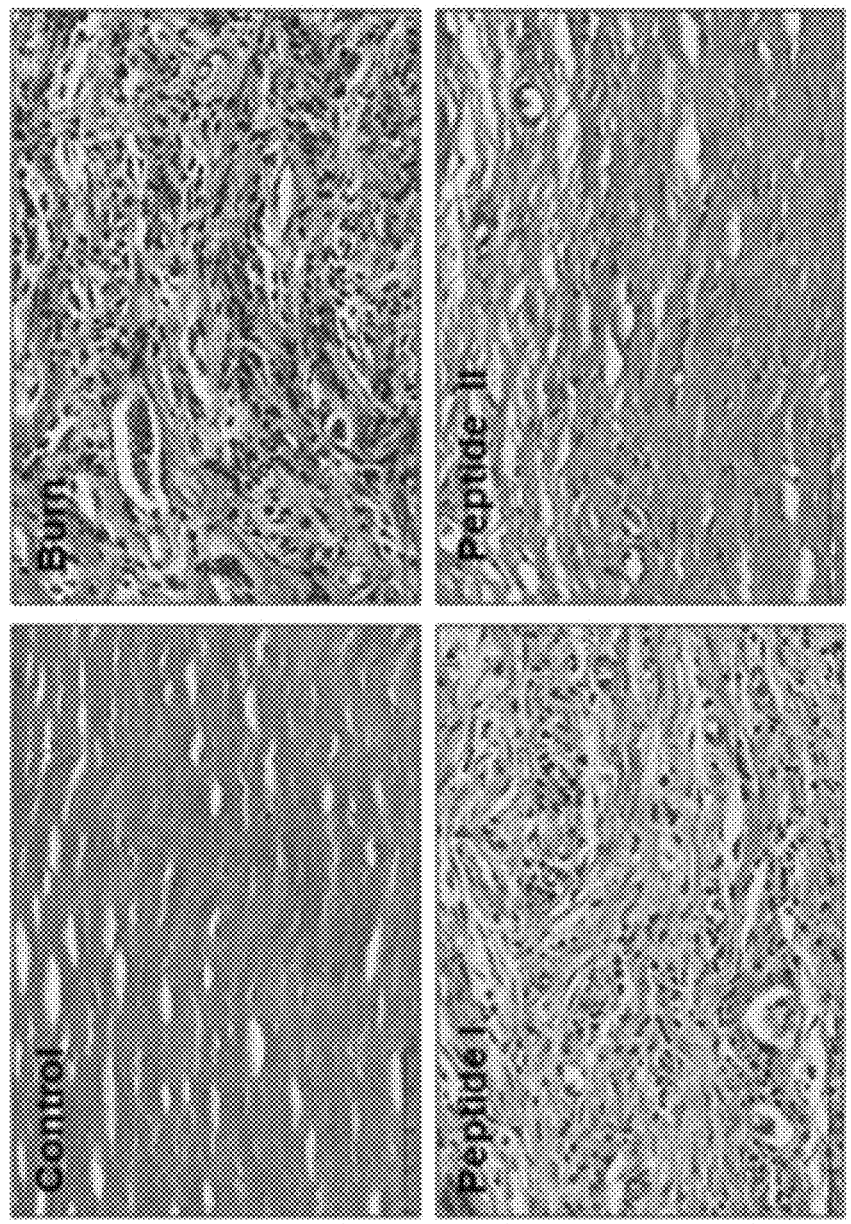
FIG. 3 shows results confirming effects of SEQ ID NO: 2 on fibrotic changes in the alkaline burn rabbit, wherein ocular fibroblasts were immunostained according to the Masson's trichrome staining method as shown in brown color. Images of the stained parts are photographed with a virtual microscope (NanoZoomer 2.0 RS, Hamamatsu, Japan) (scale bar=100 μm)

Consequently, as shown in FIG. 3, it was confirmed that alkaline burn increased formation of fibroblast with brown color in the stroma in the control group, and that peptide I treatment had little effect on the fibrotic changes upon alkaline burn. However, it was confirmed that peptide II treatment significantly suppressed the population of fibroblast.

Accordingly, it was confirmed that peptide SEQ ID NO: 2 had effects on suppressing the population of fibroblast, thereby also suppressing corneal fibrosis.

<Example 6> Confirmation of Effects of Peptide SEQ ID NO: 2 on Corneal Angiogenesis in Alkaline Burn Rabbit Histological changes in cornea following alkaline burn were observed by performing the H&E staining. The eyes were fixed in 3.5% paraformaldehyde, embedded in optimal cutting temperature compound (OCT; Tissue-Tek, Sakura Fine Technical Co., Ltd., Tokyo, Japan), and then, frozen with liquid nitrogen.

Next, the samples were fixed in 4% formaldehyde for 24 hours, dried, and then, embedded in paraffin wax. Then, tissue sections with a thickness of 8 μm were prepared and stained with hematoxylin/eosin.

First, the tissue sections having a thickness of 8 μm were stained with hematoxylin for 3 minutes and cleaned with tap water. Then, 1 or 2 drops of 1% hydrochloric acid solution were added thereto to bleach hematoxylin in the stained cytoplasm. After cleaning with water, the tissue sections were stained with eosin for 1 minute and cleaned with water. Then, through dehydration process using 85% ethanol once, 95% ethanol once, and 100% ethanol twice, the tissue sections had a reaction with carboxylene for 1 minute. After performing a process twice each using xylene solution for 3 minutes in consideration of developing transparency, the tissue sections were mounted and photographed with a virtual microscope (NanoZoomer 2.0 RS, Hamamatsu, Japan).

Figure 4:
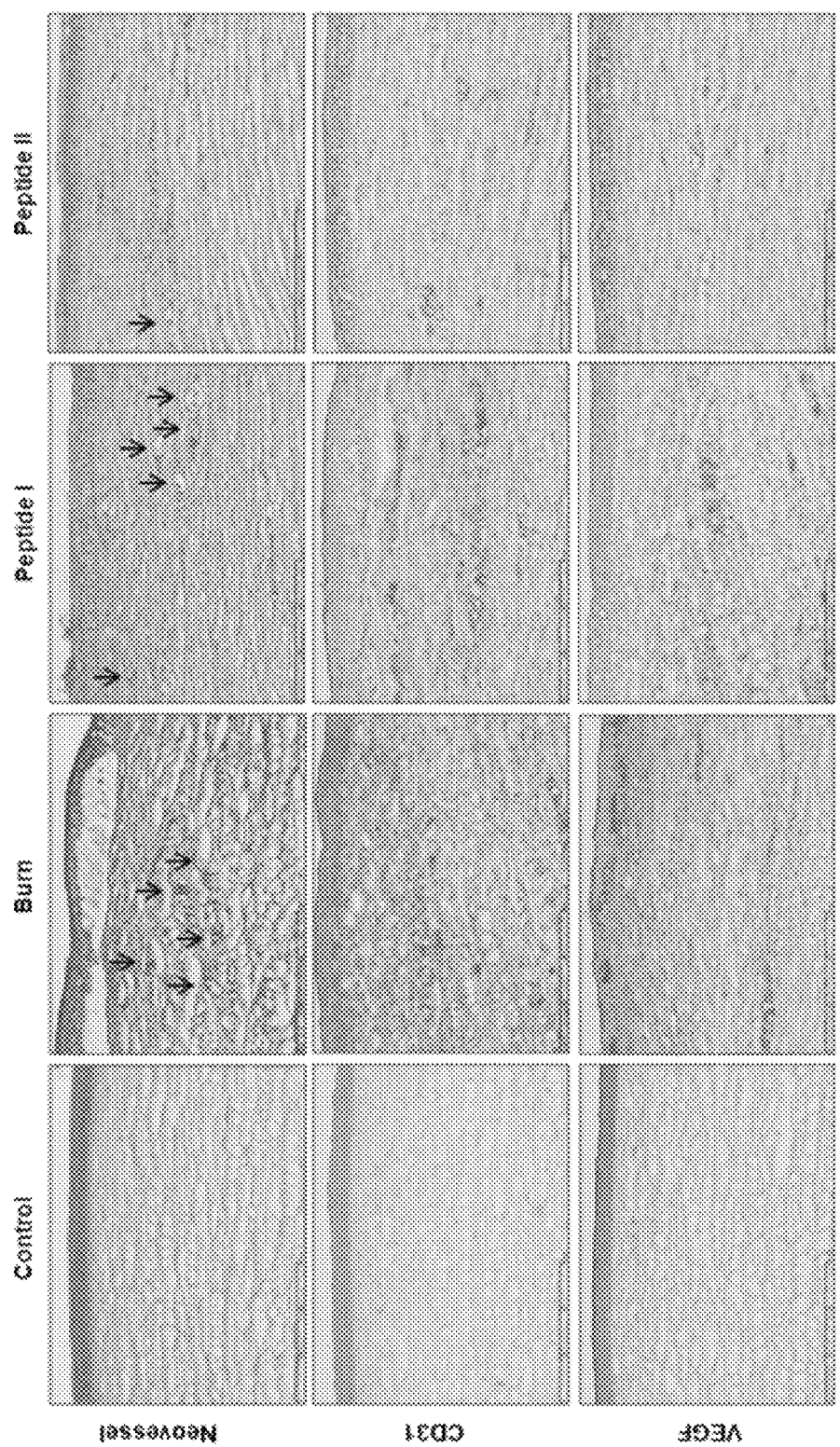
FIG. 4 shows results confirming effects of SEQ ID NO: 2 on angiogenic markers in the alkaline burn rabbit, wherein the arrows (↓) in the pictures denotes new vessels stained with the haematoxylin and eosin (H&E), and tissue sections immunostained with specific antibodies CD31 and VEGF are photographed with a virtual microscope (NanoZoomer 2.0 RS, Hamamatsu, Japan) (scale bar=300 μm)

Consequently, as shown in upper pictures of FIG. 4, it was confirmed that alkaline burn induced epithelial proliferation on cornea, infiltration of inflammatory cells, stromal edema, and angiogenesis. However, in FIG. 3, these histological alterations were improved by peptide II treatment, but the peptide I treatment had little effect on these changes.

Accordingly, it was confirmed that peptide II had effects on angiogenesis, and thus, to identify features of angiogenesis according to different peptide treatment on alkaline burn corneas, corneal angiogenesis-specific markers, e.g., CD31 and VEGF, were used for immunohistochemistry in the same manner as in Experimental Example 1.

Consequently, as shown in FIG. 4, it was confirmed that angiogenic markers, e.g., CD31 and VEGF, were strongly expressed in the fibrotic stromal cells following the alkaline burn. However, it was also confirmed that the expression of CD31 and VEGF in epithelium, subepithelium, and stroma were significantly decreased by peptide II, compared with the expression in the peptide I group.

Consequently, it was confirmed that peptide SEQ ID NO: 2 had effects on decreasing the expression of angiogenesis factors, such as CD31 and VEGF, thereby suppressing corneal angiogenesis.

<Example 7> Confirmation of Effects of Peptide SEQ ID NO: 2 on Suppressing Inflammation in Alkaline Burn Rabbit As mentioned in the previous experiments, the results of the H&E staining confirmed invasion of inflammatory cells into cornea following alkaline burn. Thus, to confirm effects of each peptide on the expression of inflammatory markers, corneal sections were immunostained with inflammation specific markers including macrophages, TNFα, ICAM-1, VCAM-1, and MMP-9 in the same manner as in Experimental Example 1.

Figure 5:
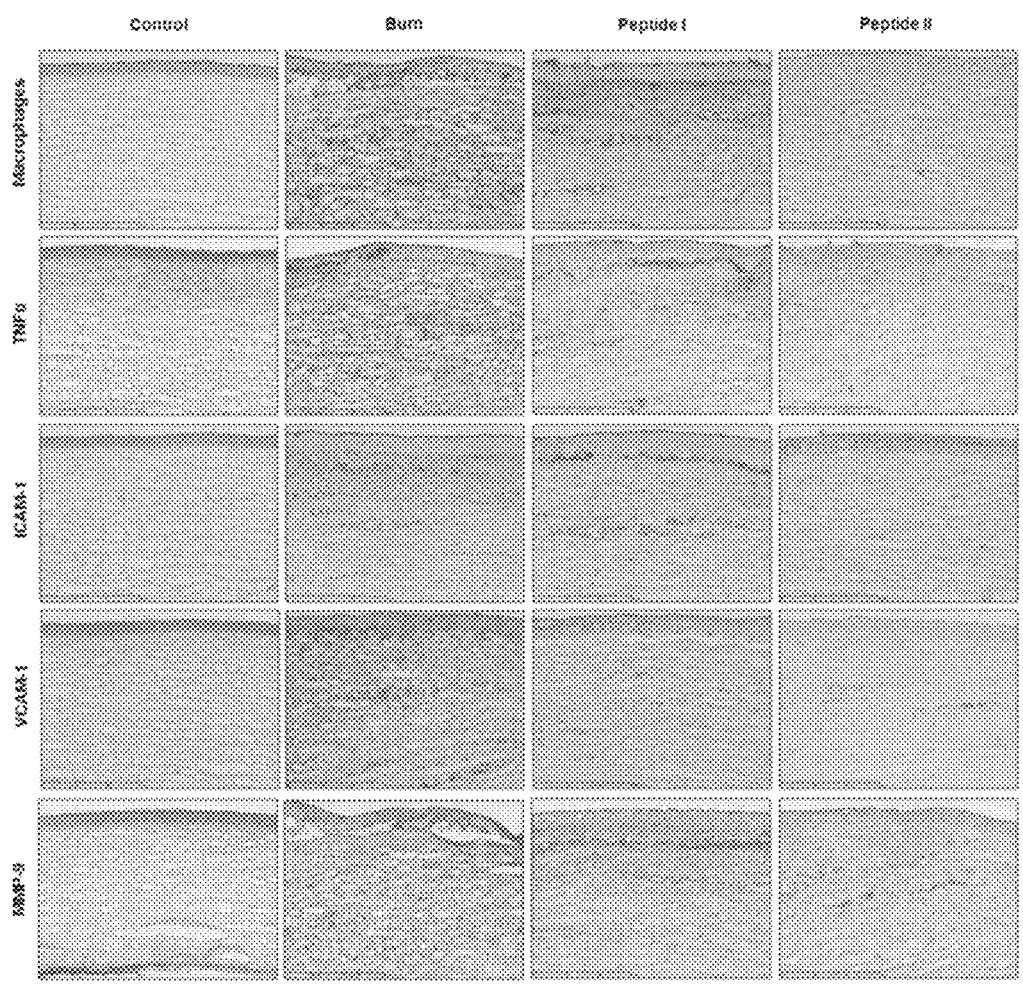
FIG. 5 shows results conforming effects of SEQ ID NO: 2 on inflammatory markers in the alkaline burn rabbit, wherein tissue sections are immunostained with specific antibodies including macrophages, TNFα, ICAM-1, VCAM-1, and MMP-9 and photographed with a virtual microscope (NanoZoomer 2.0 RS, Hamamatsu, Japan) (scale bar=300 μm)

Consequently, as shown in FIG. 5, it was confirmed that alkaline burn increased the expression of macrophages in epithelium, subepithelium, and proliferative stroma, whereas the expression of macrophages was effectively suppressed by peptide II treatment. In addition, it was confirmed that expression of inflammatory cytokine TNFα and adhesion molecules including ICAM-1 and VCAM-1 was increased in the alkaline burn group. However, expression of these inflammatory factors was decreased in the peptide II group. Furthermore, expression of MMP-9 was strongly induced in the alkaline burn group, whereas expression of MMP-9 was suppressed in the peptide II group compared to the peptide I group.

In addition, to confirm whether peptide SEQ ID NO: 2 was capable of decreasing activation of NF-κB, which is an inflammation inducing factor activated by alkaline burn, the tissue sections were immunostained with a specific antibody NF-κB in the same manner as in Experimental Example 1.

Figure 6:
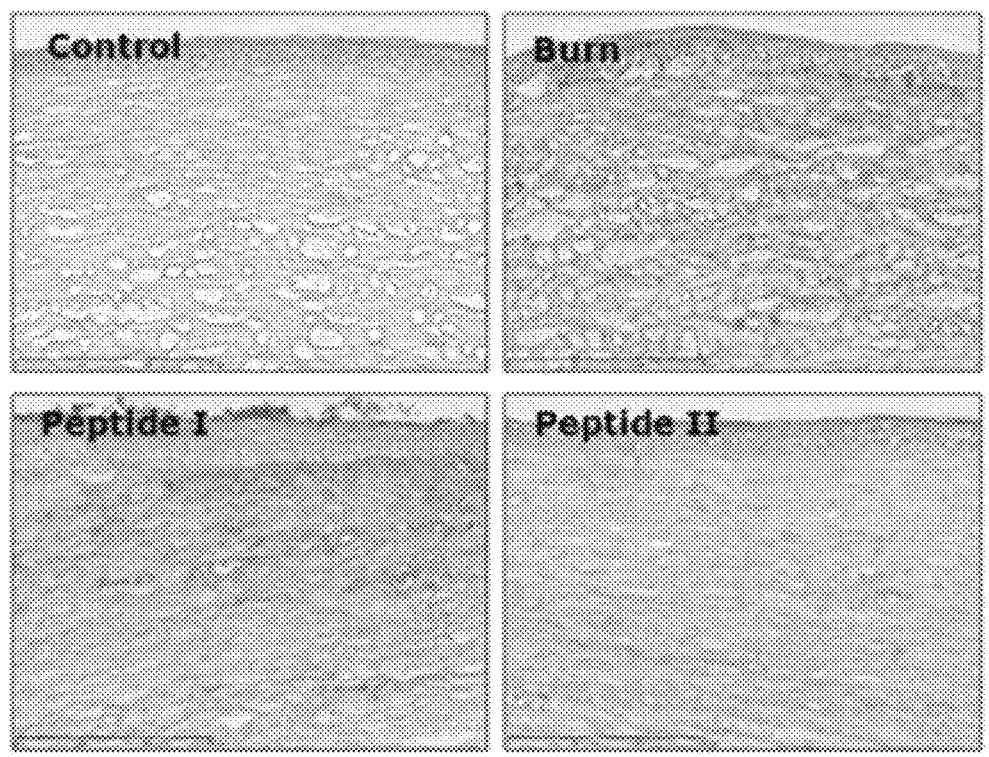
FIG. 6 shows results conforming effects of SEQ ID NO: 2 on expression of nuclear transcription factors in the alkaline burn rabbit, wherein tissue sections are immunostained with a specific antibody including NF-κB and photographed with a virtual microscope (NanoZoomer 2.0 RS, Hamamatsu, Japan) (scale bar=300 μm).

Consequently, as shown in FIG. 6, it was confirmed that expression of NF-κB was induced in stroma following alkaline burn, whereas expression of NF-κB was decreased by peptide II treatment compared to peptide I treatment.

Accordingly, it was confirmed that peptide SEQ ID NO: 2 had effects on suppressing expression of inflammatory factors, thereby affecting treatment of corneal inflammatory diseases.

composition for preventing or treating an ocular surface disease, such as corneal angiogenesis, corneal inflammation, corneal opacification, and corneal fibrosis.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Collagen type I, alpha 1

<400> SEQUENCE: 1

Gly Asp Arg Gly Asp
1               5

<210> SEQ ID NO 2
<211> LENGTH: 9
<212> TYPE: PRT
<213> ORGANISM: Artificial Sequence
<220> FEATURE:
<223> OTHER INFORMATION: Collagen type II, alpha 1

<400> SEQUENCE: 2

Gly Gln Asp Gly Leu Ala Gly Pro Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Collagen type I, alpha 1

<400> SEQUENCE: 3

Gly Pro Ala Gly Pro Arg
1               5
```

According to one or more embodiments of the present invention, as a result of administrating CDEM-derived collagen type II α1 based peptide SEQ ID NO: 2 into an animal model having an ocular surface disease induced by alkaline burn, it is confirmed that peptide SEQ ID NO: 2 decreases ocular opacity compared to ocular opacity in a control group treated with saline and a comparative group treated with peptide SEQ ID NO: 1, and expression of angiogenic factors including CD31 and VEGF. In addition, it is confirmed that peptide SEQ ID NO: 2 suppresses formation of fibroblast in stroma, decreases expression of inflammatory markers including macrophages, TNFα, ICAM-1, VCAM-1, and MMP-9, and suppresses expression of an inflammation inducing factor NF-κB. Therefore, peptide SEQ ID NO: 2 of the present invention can be applied to a pharmaceutical

What is claimed is:

1. A method of treating an ocular surface disease in a subject in need thereof, comprising;
   providing a pharmaceutical composition comprising, as an active component, a peptide comprising the sequence of SEQ ID NO: 2; and
   administering the pharmaceutical composition to the subject having a chemical burn to an eye, wherein the ocular surface disease is treated,
   wherein the ocular surface disease is selected from the group consisting of corneal opacification, corneal angiogenesis, corneal inflammation, and corneal fibrosis.

2. The method of claim 1, wherein an amount of the peptide in the pharmaceutical composition is in a range of about 0.1 to about 50 parts by weight based on a total of 100 parts by weight of the pharmaceutical composition.

3. The method of claim 1, wherein a formulation of the pharmaceutical composition is selected from the group consisting of eye drops, injections, granules, tablets, pills, capsules, gels, syrups, suspensions, emulsions, drips, and liquids.

* * * * *